United States Patent [19]
Derrieu et al.

[11] Patent Number: 5,595,762
[45] Date of Patent: Jan. 21, 1997

[54] STABILIZED PULVERULENT ACTIVE AGENTS, COMPOSITIONS CONTAINING THEM, PROCESS FOR OBTAINING THEM AND THEIR APPLICATIONS

[75] Inventors: Guy Derrieu, Cagnes sur Mer; Bernard Raynier, Nice, both of France

[73] Assignee: Laboratoires Virbac, Carros, France

[21] Appl. No.: 159,120

[22] Filed: Nov. 30, 1993

[30] Foreign Application Priority Data

Nov. 30, 1992 [FR] France ................... 92/14365

[51] Int. Cl.⁶ .................................................. A61K 9/16
[52] U.S. Cl. .................. 424/490; 424/494; 424/497; 424/498; 424/495; 514/772.2; 514/772.3; 514/772.6; 514/777; 514/778; 514/781; 514/783; 514/770; 514/951; 514/785
[58] Field of Search ...................... 424/461, 462, 424/479, 480, 482, 490, 494, 493, 495, 497, 498

[56] References Cited

U.S. PATENT DOCUMENTS

| | | | |
|---|---|---|---|
| 4,513,019 | 4/1985 | Brancq et al. | 427/3 |
| 4,687,660 | 8/1987 | Baker et al. | 424/465 |
| 4,769,027 | 9/1988 | Baker et al. | 424/493 |
| 4,917,900 | 4/1990 | Jones et al. | 424/493 |
| 5,178,868 | 1/1993 | Malmqvist-Granlund et al. | 424/490 |

FOREIGN PATENT DOCUMENTS

| | | |
|---|---|---|
| 1142084 | 3/1983 | Canada. |
| 2447720 | 8/1980 | France. |
| 2548675 | 1/1985 | France. |
| 2657255 | 7/1991 | France. |
| 2133983 | 8/1984 | United Kingdom. |

*Primary Examiner*—James M. Spear
*Attorney, Agent, or Firm*—Lowe, Price, LeBlanc & Becker

[57] ABSTRACT

Stabilized pulverulent active agents, compositions containing them and also process for obtaining them; such stabilized active agents enable dry and stable pharmaceutical, dietary, nutritional or cosmetic compositions to be obtained, in which the properties of the said active agents are neither modified nor impaired. Such stabilized active agents are stabilized by coating with a coating composition comprising:

— at least one film-forming agent, in proportions of between 2 and 25% by weight of the final mass, selected from polyvinylpyrrolidones (povidone), polyvinyl alcohols, vinylpyrrolidone/vinyl acetate copolymer, vinylpyrrolidone/polyvinyl alcohol copolymer, cellulose derivatives such as cellulose acetate, cellulose acetate phthalate, cellulose butyrate, ethylcellulose and methylcellulose, acrylic and methacrylic polymers and copolymers and vegetable, animal or synthetic waxes, and — at least one pore-forming agent, in proportions of between 0 and 5%, by weight preferably of between 0.5 and 5%, of the final mass, selected from microcrystalline lactose, low molecular weight polyethylene glycols, calcium carbonate, calcium phosphate, sucrose, sodium chloride and potassium chloride.

The stabilized pulverulent active product, in the form of microparticles, possesses a particle size of between 50 and 1000 μm, and preferably between 200 and 500 μm.

7 Claims, No Drawings

STABILIZED PULVERULENT ACTIVE AGENTS, COMPOSITIONS CONTAINING THEM, PROCESS FOR OBTAINING THEM AND THEIR APPLICATIONS

The present invention relates to stabilized pulverulent active agents, to compositions containing them and also to a process for obtaining them; such stabilized active agents enable dry and stable pharmaceutical, dietary, nutritional or cosmetic compositions to be obtained, in which the properties of the said active agents are neither modified nor impaired.

For the purposes of the present invention, active agent is understood to mean any chemical substance capable of being transformed, degraded or impaired through the influence of a physical, mechanical or thermal manipulation of any kind, especially under pressure and in the presence of water.

In effect, such transformations do not enable the integrity of the active agents to be maintained during the production and storage over time of manufactured products such as mixtures of powders and granulated or compacted compositions.

The presentation of many active agents in the form of spherical or non-spherical granules or microcapsules which are coated in order, among other advantages, to facilitate their flow and transfer, to avoid inter-particle adhesion or to obtain delayed-release effects, is known to a person skilled in the art.

Microcapsules, in particular, are generally prepared according to the simple coacervation process, in which a polymer is separated from a solution of the polymer in a solvent, either by evaporation of the said solvent, or by the action of a precipitating agent (salt or non-solvent for the said polymer). Another technique involves a microencapsulation based on a polymerization by in situ interfacial condensation.

However, such coatings are not suited to the stabilization, without modification of the physical characteristics, especially the solubility, the lipophilic nature and the crossing of the different physiological barriers, of the active agents treated.

The present invention was consequently directed towards the objective of providing for stabilized active agents, as well as for pulverulent compositions containing these stabilized agents; in effect, stabilization makes it possible to avoid all impairment of these active agents during the formulation operations, such as granulation or compaction, for putting them in their final form (pharmaceutical, dietary, nutritional or cosmetic), and assures the integrity of the active agents throughout the life of the manufactured products obtained without modifying their activity and their physical properties.

The subject of the present invention is pulverulent active agents stabilized by coating with a coating composition of the type comprising at least one film-forming agent, characterized:

(i) in that the said coating composition comprises:
— at least one film-forming agent, in proportions of between 2 and 25% by weight of the final mass, selected from polyvinylpyrrolidones (povidone), polyvinyl alcohols, vinylpyrrolidone/vinyl acetate copolymer, vinylpyrrolidone/polyvinyl alcohol copolymer, cellulose derivatives such as cellulose acetate, cellulose acetate phthalate, cellulose butyrate, ethylcellulose and methylcellulose, acrylic and methacrylic polymers and copolymers and vegetable waxes (Carnauba, Candelilla, etc.), animal waxes (beeswax, hydrogenated castor oil, etc.) or synthetic waxes (ethylenic polymers, polyol ether ester such as Carbowax®, etc.), and
— at least one pore-forming agent, in proportions of between 0 and 5%, preferably of between 0.5 and 5%, by weight of the final mass, selected from microcrystalline lactose, low molecular weight polyethylene glycols, calcium carbonate, calcium phosphate, sucrose, sodium chloride and potassium chloride, (ii) and in that the stabilized pulverulent active product in the form of microparticles possesses a particle size of between 50 and 1000 µm, and preferably between 200 and 500 µm.

The said active agents are preferably coated by spraying the said coating composition, in solution, suspension or emulsion in a vehicle or mixture of vehicles which is/are inert with respect to the active agent, onto the said active agent in pulverulent form.

The said coating composition comprising a film-forming agent in proportions of between 2 and 25% by weight of the final mass, and preferably between 5 and 15%, and eventually a pore-forming agent in proportions of between 0.5 and 5% by weight of the final mass, is capable of forming a uniform film at the surface of the pulverulent active agents.

These stabilized active agents in pulverulent form, that is to say coated in a coating composition comprising at least one film-forming agent and at least, eventually, one pore-forming agent, form microparticles in which the active agents are protected effectively against subsequent physical treatments (in particular heat), processed for putting them in their final form (in particular granulation and compaction), while not modifying their physical properties (solubility, lipophilic nature).

In addition, the combination of film-forming agent and pore-forming agent enables a coating composition to be obtained whose polymer structure (film-forming agent) is modified by the presence of the pore-forming agent; such a coating composition consequently possesses the following special characteristics:

during the step of preparation of the granulated or compacted compositions comprising the said stabilized active agents in the form of microparticles: resistance of the said coating composition during the granulation operation (even in the presence of water vapour), since the pore-forming agent, whose structure is essentially crystalline, is not modified during this operation (no dissolution of the pore-forming agent); consequently, there is no destruction of the coating and the active agent is well protected; in effect, such stabilized active agents are not degraded during the operation of granulation by extrusion in particular, in which the joint action of solvents and of high temperatures, preferably in the presence of water or water-vapour, with or without a pressure generator, may be involved; whereas on oral administration of the said granulated or compacted compositions comprising the said coated active agents, there is rapid destruction of the said coating composition as a result of the presence of the said pore-forming agent, constituting preferential points of access to biological fluids.

The active agents coated with a coating composition according to the invention, apart from the fact that they are stabilized, surprisingly retain the property of solubilizing normally, that is to say at the same rate as the uncoated active agent (absence of delayed-release effect).

According to an advantageous embodiment of the invention, prior to their coating with the said coating composition, the said active agents may be combined with a sequestering agent.

The sequestering agents are, in particular, chosen from carbohydrates or polysaccharides such as cellulose, dextrins, cyclodextrins, starch, dextrans, etc.

The film-forming agent and, where appropriate, the pore-forming agent and the sequestering agent are chosen according to the nature of the active agent to be stabilized, this in no case resulting in modification of the abovementioned physical characteristics of the active agent.

The active agents are preferably chosen from the following families:

— vitamins such as thiamine (salts and derivatives), pyridoxine (salts and derivatives), cobalamine and derivatives, menadione and derivatives, folic acid and derivatives, ascorbic acid (salts and derivatives), nicotinic acid, nicotinamide, and the like, — amino acids and proteins, — trace elements (selenium and its salts, copper and its salts, and the like), — antibiotics such as macrolides, tetracyclines, penicillins, cephalosporins, aminoglycosides, — synthetic anti-infectious agents, — antiparasitic agents, — growth factors, — other antibacterial agents, — antifungal agents, — antiseptics, and the like.

According to another advantageous embodiment of the invention, the coating composition comprises, in addition, at least one other constituent chosen from plasticizers and antiadhesive agents.

According to an advantageous arrangement of this embodiment, the plasticizers are chosen from glycerol and its esters, high molecular weight polyethylene glycols, castor oil and citric, phthalic, adipic and sebacic acid esters.

According to another advantageous arrangement of this embodiment, the antiadhesive agents are preferably chosen from talc, colloidal silica and magnesium stearate.

According to yet another advantageous embodiment of the said coated active agent (microparticles), it comprises at least 50% of active agent.

The subject of the present invention is also granulated or compacted compositions, characterized in that they comprise at least one pulverulent stabilized active agent as defined above.

The stabilized active agents according to the invention and the granulated or compacted compositions (including mixtures of powders) containing them find application in the pharmaceutical, veterinary, dietary, nutritional or cosmetics field.

The subject of the present invention is also a process for the stabilization of active agents, characterized:

— in that a coating composition is prepared by dissolution, suspension, or emulsification, in a vehicle or mixture of vehicles which is/are inert with respect to the active agent, of:

at least one film-forming agent, in proportions of between 2 and 25% by weight of the final mass, selected from polyvinylpyrrolidones (povidone), polyvinyl alcohols, vinylpyrrolidone/vinyl acetate copolymer, vinylpyrrolidone/polyvinyl alcohol copolymer, cellulose derivatives such as cellulose acetate, cellulose acetate phthalate, cellulose butyrate, ethylcellulose and methylcellulose, acrylic and methacrylic polymers and copolymers and vegetable waxes (Carnauba, Candelilla, etc.), animal waxes (beeswax, hydrogenated castor oil, etc.) or synthetic waxes (ethylenic polymers, polyol ether ester such as Carbowax®, etc.), and at least one pore-forming agent, in proportions of between 0 and 5%, preferably of between 0.5 and 5%, by weight of the final mass, selected from microcrystalline lactose, low molecular weight polyethylene glycols, calcium carbonate, calcium phosphate, sucrose, sodium chloride and potassium chloride, — in that the active agent in pulverulent form is coated with the said coating composition in solution, suspension or emulsion, — and in that a stabilized pulverulent active agent, coated in the said coating composition (microparticles), possessing a particle size of between 50 and 1,000 μm and preferably between 200 and 500 μm, is obtained.

According to an advantageous embodiment of the said process, the coating is carried out by spraying in an air-fluidized bed.

According to another advantageous embodiment of the said process, the coating is carried out by nebulization.

The invention also includes, as a coating technique, any other technique enabling the same result to be obtained (homogeneous film, physical properties retained).

Prior to the said coating, the coating composition is advantageously in solution, suspension or emulsion in a vehicle or mixture of vehicles which is/are inert with respect to the active agent to be coated, as specified above. The choice of vehicle, used alone or in combination, is dependent on the properties of the film-forming agent and, where appropriate, of the pore-forming agent and of the sequestering agent used.

The vehicles are preferably chosen from water, halogenated hydrocarbons such as methylene chloride, chloroform, dichloroethane, etc., alcohols such as methanol, ethanol, propanol and isopropanol and acetone.

According to the invention, prior to the coating, the said coating composition is combined with at least one other constituent chosen from plasticizers and antiadhesive agents as defined above.

Apart from the foregoing arrangements, the invention also comprises other arrangements which will become apparent from the description which follows, in which reference is made to examples of compositions and of embodiments of the process which are subjects of the present invention.

It should, however, be clearly understood that these examples are given only by way of illustration of the subject of the invention and in no way constitute a limitation of the latter.

EXAMPLE 1: Preparation of microparticles of furaltadone (active agent) stabilized with a coating composition comprising povidone as film-forming agent and sodium chloride as pore-forming agent (coating by treatment in an air-fluidized bed).

3 kg of furaltadone are suspended in a GLATT WSG5 granulator and treated with a solution of povidone, 220 g, and of sodium chloride, 30 g, at a concentration of 6% m/v in an aqueous-alcoholic medium (water/ethanol, 80:20).

The treatment is performed under the following conditions:

— spray output 40 ml/min,

— atomization pressure 1.2 to 1.4 bar,
— temperature in the chamber 50° to 55° C.,
— temperature of the product 30° to 35° C.,
— air flow rate 1.5 to 2 m³/min.

When spraying has finished, the air flow is maintained under the same temperature and pressure conditions for 45 to 60 minutes to ensure that the product is well dried. The product obtained possesses a particle size of between 0.2 and 0.5 mm.

EXAMPLE 2: Preparation of microparticles of ascorbic acid stabilized with a coating composition comprising dextrin as sequestering agent, polymethacrylate as film-forming agent and sucrose as pore-forming agent (coating by nebulization).

A homogeneous mixture of 250 g of ascorbic acid and 50 g of dextrin is suspended in 2 liters of methylene chloride containing 40 g of polymethacrylate and 10 g of sucrose. Atomization is carried out on a MINOR MOBILE ATOMIZER (NIRO-ATOMIZER) equipped with an upward jet nozzle, under the following conditions:

— feed rate 30 ml/min,
— pressure from 3 to 3.2 bar,
— temperature of the chamber 28° to 32° C.

The product obtained has a particle size of between 0.08 and 0.2 mm (microparticles 2A).

Microparticles of acid ascorbic stabilized with a coating composition without pore-forming agent may also be obtained in the same conditions (microparticles 2B).

EXAMPLE 3: Preparation of microparticles of amoxycillin stabilized with a coating composition containing povidone as film-forming agent, lactose as pore-forming agent and a plasticizer and an antiadhesive agent as other constituents (coating by treatment in an air-fluidized bed).

3 kg of amoxycillin trihydrate are suspended in a GLATT WSG5 granulator and treated with a solution of povidone, 180 g, at a concentration of 6% m/v in an aqueous-alcoholic medium (water/ethanol, 80:20) in the presence of 35 g of lactose, 30 g of dibutyl phthalate and 5 g of colloidal silica.

The treatment is performed under the following conditions:

— spray output 40 ml/min,
— atomization pressure 1.2 to 1.4 bar,
— temperature in the chamber 50° to 55° C.,
— temperature of the product 30° to 35° C.,
— air flow rate 1.5 to 2 m³/min.

When spraying has finished, the air flow is maintained under the same temperature and pressure conditions for 45 to 60 minutes to ensure that the product is well dried. The product obtained possesses a particle size of between 0.2 and 0.5 mm (microparticles 3A).

Microparticles of amoxycillin stabilized with a coating composition without pore-forming agent may also be obtained in the same conditions (microparticles 3B).

EXAMPLE 4: Preparation of a composition which is granulated by extrusion, comprising microparticles according to Example 3.

The microparticles according to Example 3 (microparticles 3A and 3B) are converted in a conventional manner into granules by extrusion, in the presence of vegetable flours such as wheat or soya flour. This manufacture involves operations of mixing in the dry state and then in the presence of water, compression in the presence of water vapour and drying.

The granules containing 400 ppm of amoxycillin, stored under normal conditions of temperature (approximately 22° C.) and humidity (approximately 70%) in the packing in which it is sold (paper bag), are analysed periodically; in parallel, granules produced in the same manner with unstabilized amoxycillin, stored under the same conditions, are analysed. The results are collated in Table I below:

TABLE I

| Storage period | Initial | 20 days | 43 days | 100 days | 170 days |
| --- | --- | --- | --- | --- | --- |
| amoxycillin content, Granules according to the invention | 411 | 398 | 404 | 399 | 396 |
| amoxycillin content, Reference granules | 323 | 285 | 226 | 167 | 132 |

This experiment demonstrates the stability of the active agent (amoxycillin) in a manufactured product (granules) employing stabilized amoxycillin (microparticles) according to the invention.

EXAMPLE 5: Test of in vitro availability.

A test of in vitro availability of the amoxycillin from the granules prepared according to Example 4 (microparticles 3A and 3B) was carried out in comparison with amoxycillin granules (reference granules 1) prepared with unstabilized amoxycillin (traditional manufacture):

TABLE II

| Dissolution time | 30 s | 1 min | 5 min | 10 min |
| --- | --- | --- | --- | --- |
| % of amoxycillin solubilized, Granules 3A of Example 4 | 51 | 63 | 96 | 100 |
| % of amoxycillin solubilized, Granules 3B of Example 4 | 40 | 61 | 96 | 100 |
| % of amoxycillin solubilized, Reference granules 1 | 50 | 59 | 95 | 100 |

This experiment shows that the availability of the active agent (amoxycillin) in a manufactured product (granules) produced according to the invention is in all respects equivalent to that of a granule containing the same active agent uncoated; this shows clearly that the physical characteristics of the active agent are not modified by the protective coating; in addition, in particular for very short times, the presence of a pore-forming agent permits solubilization of the active agent at the same rate as that of the uncoated active agent.

EXAMPLE 6: Further test of in vitro availability.

A test of in vitro availability of the ascorbic acid in a mixture of powders (A) prepared from the microcapsules 2A according to Example 2 was carried out in comparison with a mixture of powders (B) prepared from microparticles 2B according to Example 2 and in comparison with a mixture of powders (C) prepared with unstabilized (uncoated) ascorbic acid. The results are collated in Table III.

TABLE III

| Dissolution time | 30 s | 1 min | 5 min |
| --- | --- | --- | --- |
| % of ascorbic acid solubilized, Mixture of powders (A) | 85 | 98 | 100 |
| % of ascorbic acid solubilized, Mixture of powders (B) | 65 | 91 | 100 |
| % of ascrobic acid solubilized, Mixture of powders (C) | 98 | 100 | |

This experiment shows that the availability of the active agent (ascorbic acid) in a mixture of powders prepared with microparticles according to the invention is in all respects equivalent to that of a mixture of powders containing the same active agent uncoated.

As is apparent from the foregoing, the invention is in no way limited to those modes of implementation, embodiments and modes of application which have just been described more explicitly; it encompasses, on the contrary, all variants thereof which may occur to the expert in the field, without departing from the scope or the range of the present invention.

We claim:

1. Microparticles of pulverulent active agent adapted for formulation manufacturing process physical treatments, wherein said pulverulent active agent comprises for its stabilization, an immediate release coating consisting essentially of (a) at least one film-forming agent, in proportions of between 2 and 25% by weight of the final mass, selected from the group consisting of polyvinylpyrrolidones (povidone), polyvinyl alcohols, vinylpyrrolidone/vinyl acetate copolymer, vinylpyrrolidone/polyvinyl alcohol copolymer, cellulose acetate, cellulose acetate phthalate, cellulose butyrate, ethylcellulose, methylcellulose, acrylic and methacrylic polymers and copolymers and vegetable, animal or synthetic waxes, and (b) at least one pore-forming agent, in proportions of between 0.5 and 5% by weight of the final mass, selected from the group consisting of microcrystalline lactose, low molecular weight polyethylene glycols, calcium carbonate, calcium phosphate, sucrose, sodium chloride and potassium chloride, and leading to microparticles having a particle size of between 50 and 100 µm.

2. Microparticles of pulverulent active agent according to claim 1, wherein said pulverulent active agent further comprises a sequestering agent selected from the group consisting of cellulose, dextrins, cyclodextrins, starch, dextrans.

3. Microparticles of pulverulent active agent according to claim 1, wherein said coating further comprises at least one constituent selected from the group consisting of (a) plasticizers selected from the group consisting of glycerol and its esters, high molecular weight polyethylene glycols, castor oil and citric, phthalic, adipic and sebacic acid esters, and (b) antiadhesive agents selected from the group consisting of talc, colloidal silica and magnesium stearate.

4. Microparticles of pulverulent active agent according to claim 1, comprising at least 50% of active agent.

5. Granulated or compacted compositions, comprising as active agent, microparticles of pulverulent active agent having a particle size of between 50 and 1000 µm, said microparticles being obtained by coating said pulverulent active agent with an immediate release coating consisting essentially of (a) at least one film-forming agent, in proportions of between 2 and 25% by weight of the final mass, selected from the group consisting of polyvinyl-pyrrolidones (povidone), polyvinyl alcohols, vinylpyrrolidone/vinyl acetate copolymer, vinylpyrrolidone/polyvinyl alcohol copolymer, cellulose acetate, cellulose acetate phthalate, cellulose butyrate, ethylcellulose, methylcellulose, acrylic and methacrylic polymers and copolymers and vegetable, animal or synthetic waxes, and (b) at least one pore-forming agent, in proportions of between 0.5 and 5% by weight of the final mass, selected from the group consisting of microcrystalline lactose, low molecular weight polyethylene glycols, calcium carbonate, calcium phosphate, sucrose, sodium chloride and potassium chloride.

6. Microparticles of pulverulent active agent according to claim 1, wherein said microparticles have a particle size of between 200 and 500 µm.

7. Microparticles of claim 1, wherein said microparticles do not exhibit a delayed release effect.

* * * * *

UNITED STATES PATENT AND TRADEMARK OFFICE
CERTIFICATE OF CORRECTION

PATENT NO. : 5,595,762
DATED : January 21, 1997
INVENTOR(S) : Guy DERRIEU ET AL

It is certified that error appears in the above-indentified patent and that said Letters Patent is hereby corrected as shown below:

In Claim 1, line 19 should read as follows:
--particle size of between 50 and 1000μm.--

Signed and Sealed this

Twenty-seventh Day of May, 1997

*Attest:*

BRUCE LEHMAN

*Attesting Officer*    *Commissioner of Patents and Trademarks*